United States Patent
Bender et al.

(10) Patent No.: US 7,846,937 B2
(45) Date of Patent: Dec. 7, 2010

(54) CYCLOPROPANECARBOXYLATE ESTERS OF ACYCLOVIR

(75) Inventors: David Michael Bender, Indianapolis, IN (US); James Ray McCarthy, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 455 days.

(21) Appl. No.: 11/912,350

(22) PCT Filed: May 4, 2006

(86) PCT No.: PCT/US2006/016830

§ 371 (c)(1),
(2), (4) Date: Oct. 23, 2007

(87) PCT Pub. No.: WO2006/127217

PCT Pub. Date: Nov. 30, 2006

(65) Prior Publication Data

US 2009/0270428 A1 Oct. 29, 2009

Related U.S. Application Data

(60) Provisional application No. 60/684,493, filed on May 25, 2005.

(51) Int. Cl.
*C07D 473/18* (2006.01)
*A61K 31/522* (2006.01)
*A61P 31/22* (2006.01)

(52) U.S. Cl. .................... 514/263.38; 544/276

(58) Field of Classification Search ............... 544/276; 514/263.38
See application file for complete search history.

(56) References Cited

U.S. PATENT DOCUMENTS

| | | | |
|---|---|---|---|
| 4,199,574 A | 4/1980 | Schaeffer | |
| 4,548,819 A | 10/1985 | De Clercq et al. | |
| 4,957,924 A | 9/1990 | Beauchamp et al. | |
| 5,543,414 A * | 8/1996 | Nestor et al. ........... | 514/263.38 |
| 5,879,706 A | 3/1999 | Carter et al. | |
| 6,107,302 A | 8/2000 | Carter et al. ........... | 514/249 |
| 2003/0114460 A1 * | 6/2003 | Hughes et al. ........... | 514/249 |

FOREIGN PATENT DOCUMENTS

| | | |
|---|---|---|
| EP | 0308065 B1 | 1/1995 |
| WO | WO 2009111739 A2 * | 9/2009 |

OTHER PUBLICATIONS

Hovgaard et al., Drug Delivery Studies in Caco-2 Monolayers. Synthesis, Hydrolysis, and Transport of O-Cyclopropane Carboxylic Acid Ester Prodrugs of Various β-Blocking Agents, *Pharmaceutical Research*, 1995, 387-392, vol. 12, No. 3.
Colla et al., Synthesis and Antiviral Activity of Water-Soluble Esters of Acyclovir [9-[(2-Hydroxyethoxy)methyl]guanine], *J. Med. Chem.*, 1983, 602-604, vol. 26.
Anand et al., Novel dipeptide prodrugs of acyclovir for ocular herpes infections: Bioreversion, antiviral activity and transport across rabbit cornea, *Current Eye Research*, 2003, 151-163, vol. 26, No. 3-4.
Salaun et al., Biologically Active Cyclopropanes and Cyclopropenes, *Current Medicinal Chemistry*, 1995, 511-542, vol. 2.
Stammer, Cyclopropane Amino Acids (2,3- and 3,4-Methanoamino Acids), *Tetrahedron*, 1990, 2231-2254, vol. 46, No. 7.
Onishi et al., A practical synthesis of antiviral cyclopropane nucleoside A-5021, *Tetrahedron Letters*, 1999, 8845-8847, vol. 40.
Dzolic et al., Synthesis, Structural Studies, and Biological Evaluation of some Purine Substituted 1-Aminocyclopropane-l-carboxylic Acids and 1-Amino-lhydroxymethylcyclopropanes, *Nucleosides, Nucleotides & Nucleic Acids*, 2003, 373-389, vol. 22, No. 4.

* cited by examiner

*Primary Examiner*—Mark L Berch
(74) *Attorney, Agent, or Firm*—Mark A. Winter

(57) ABSTRACT

The present invention provides compounds of Formula (I), pharmaceutical compositions thereof, methods of using the same, processes for preparing the same, and intermediates thereof.

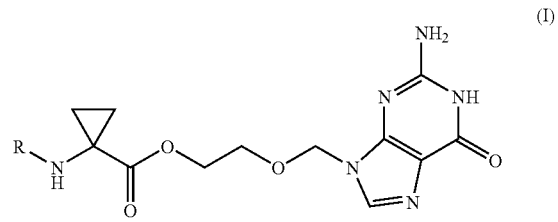

7 Claims, No Drawings

CYCLOPROPANECARBOXYLATE ESTERS OF ACYCLOVIR

This application is a United States national phase entry, pursuant to 35 U.S.C. 371, of PCT/US2006/016830, filed May 4, 2006, which claims the benefit of U.S. provisional application Ser. No. 60/684,493, filed May 25, 2005.

The present invention provides compounds of Formula I, pharmaceutical compositions thereof, methods of using the same, processes for preparing the same, and intermediates thereof.

U.S. Pat. No. 4,199,574 describes certain substituted purines including 9-(2-hydroxyethoxymethyl)guanine, otherwise known as acyclovir, which are useful for treating viral infections. Acyclovir possesses poor water solubility which may limit formulation of the drug in aqueous pharmaceutical preparations where a solution is desired. Also, acyclovir is poorly absorbed from the gastrointestinal tract after oral administration to rats and humans. Such low bioavailability requires administration of large doses of drug in order to achieve and maintain effective anti-viral levels in the plasma.

U.S. Pat. No. 4,548,819 describes certain mono-peptide esters of acyclovir which are useful in treating virus infections. Disclosed are the glycine and alanine esters which show improved water solubility compared to acyclovir.

U.S. Pat. No. 4,957,924 describes a certain mono-peptide ester of acyclovir, 2(2-amino-1,6-didydro-6-oxo-9H(purin-9-yl)methoxy)ethyl L-valinate, otherwise known as valacyclovir, which shows increase in absorption from the gut compared with acyclovir and the glycine and alanine esters of acyclovir.

Colla et al, *J. Med. Chem.*, 26, 602-604 (1983) describes certain esters of acyclovir with antiviral activity. The glycine and alanine esters of acyclovir are readily hydrolyzed at pH 7.4 suggesting the antiviral activity is due to release of the parent compound, acyclovir.

Anand et al, *Curr. Eye Res.*, 26, 151-163 (2003) describes certain limitations of acyclovir and valacyclovir in the treatment of ocular herpes infections. Acyclovir is limited in treating herpes simplex keratitis in part due to poor corneal permeability. Valacyclovir showed improved corneal permeability compared to acyclovir. However, valacyclovir showed poor stability in aqueous solution. The poor stability of valacyclovir renders it unsatisfactory for an ophthalmic solution. Certain dipeptide esters of acyclovir showed improved solution stability at certain pH's compared to valacyclovir.

The present invention provides compounds of Formula I

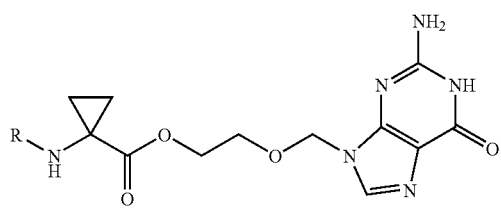

wherein R is hydrogen or $C_1$-$C_4$ alkyl.

Such compounds are certain monopeptide esters, cyclopropanecarboxylate esters of acyclovir, possessing unexpected stability.

The present invention also provides a pharmaceutically acceptable salt form of a compound of Formula I.

The present invention also provides a novel pharmaceutical composition, comprising a compound of the Formula I and a pharmaceutically acceptable carrier, diluent or excipient.

The present invention also provides a method of treating a herpes virus infection comprising administering to a patient in need thereof an effective amount of a compound of Formula I.

In a preferred embodiment the present invention provides a method of treating a herpes simplex or herpes zoster infection comprising administering to a patient in need thereof an effective amount of a compound of Formula I.

In another preferred embodiment the present invention provides a method of treating herpes simplex keratitis comprising administering to a patient in need thereof an effective amount of a compound of Formula I.

The present invention also provides the use of a compound of Formula I as a medicament.

The present invention also provides a use of the compound of Formula I for the manufacture of a medicament for treating a herpes virus infection.

The present invention also provides a process for preparing a compound of Formula I, or a pharmaceutically acceptable salt thereof, comprising:

a) for a compound of Formula I

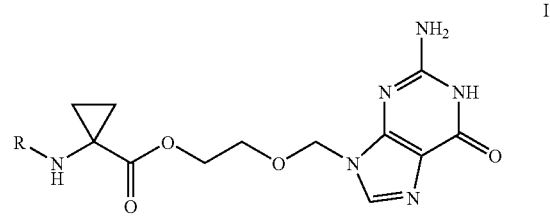

wherein R is hydrogen or $C_1$-$C_4$ alkyl deprotecting a compound of Formula II

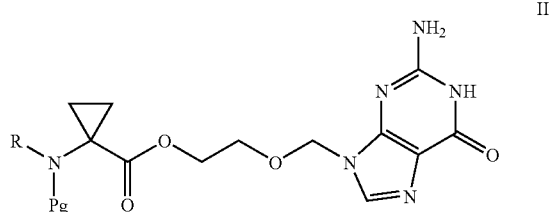

wherein R is hydrogen or $C_1$-$C_4$ alkyl, and Pg is an amine protecting group; and b) for a compound of Formula II wherein Pg is an amine protecting group acylating the compound acyclovir with a compound of Formula III

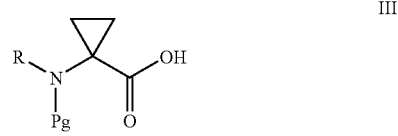

wherein R is hydrogen or $C_1$-$C_4$ alkyl, and Pg is a amine protecting group.

Before describing the present invention in greater detail, it is understood that the invention in its broadest sense is not limited to particular embodiments described herein, as variations of the particular embodiments described herein are within the scope of the claimed invention.

As used herein, the below terms have the indicated meanings.

The term "$C_1$-$C_4$ alkyl" refers to a straight or branched alkyl chain having from one to four carbon atoms, and includes methyl, ethyl, propyl, iso-propyl, butyl, iso-butyl, sec-butyl, t-butyl and the like.

The term "pharmaceutically acceptable salt" refers to an addition salt that exists in conjunction with the acidic or basic portion of a compound of Formula I. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan. Pharmaceutically acceptable salts of an acid addition nature are formed when a compound of Formula I and the intermediates described herein containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when a compound of Formula I and the intermediates described herein containing an acidic functionality are reacted with a pharmaceutically acceptable base. Pharmaceutically acceptable bases commonly employed to form base addition salts include organic and inorganic bases.

In addition to pharmaceutically acceptable salts, other salts are included in the invention. They may serve as intermediates in the purification of compounds or in the preparation of other pharmaceutically-acceptable salts, or are useful for identification, characterization or purification.

As used herein, the term "patient" refers to a warm blooded animal such as a mammal which is infected with herpes virus. A human is a preferred mammal within the scope of the meaning of the term. It is also understood that a mammal may vary to susceptibility and severity of infection.

It is also recognized that one skilled in the art may affect a herpes virus infection by treating a patient presently infected with the virus and displaying symptoms or by prophylactically treating an infected patient at risk of a future symptom outbreak with an effective amount of the compound of Formula I. Thus, the terms "treatment" and "treating" are intended to refer to all processes wherein there may be a slowing, interrupting, arresting, controlling, or stopping of the progression of the herpes virus infection and/or symptoms thereof, but does not necessarily indicate a total elimination of all symptoms or infection, and is intended to include prophylactic treatment of such.

As used herein, the term "effective amount" of a compound of Formula I refers to an amount, that is, the dosage which is effective in treating a herpes virus infection described herein.

The attending diagnostician, as one skilled in the art, can readily determine an effective amount by the use of conventional techniques and by observing results obtained under analogous circumstances. In determining an effective amount, the dose of a compound of Formula I, a number of factors are considered by the attending diagnostician, including, but not limited to the compound of Formula I to be administered; the co-administration of other antiviral agents, if used; the species of mammal; its size, age, and general health; the specific infecting virus; the degree of involvement or the severity of the infection; the response of the individual patient; the mode of administration; the bioavailability characteristics of the preparation administered; the dose regimen selected; the use of other concomitant medication; and other relevant circumstances.

An effective amount of a compound of Formula I is expected to vary from about 0.01 milligram per kilogram of body weight per day (mg/kg/day) to about 100 mg/kg/day. Preferred amounts may be determined by one skilled in the art.

The term "protecting group or Pg," as used herein, refers to those groups intended to protect or block functional groups against undesirable reactions during synthetic procedures. In the case of an amino functional group, the suitable protecting group used will depend upon the conditions that will be employed in subsequent reaction steps wherein protection is required. Commonly used amino protecting groups are disclosed in PROTECTIVE GROUPS IN ORGANIC SYNTHESIS, T. W. Greene and P. G. M. Wuts 3rd Ed. (John Wiley & Sons, New York (1999)). Suitable amino protecting groups include acyl groups such as formyl, acetyl, propionyl, pivaloyl, and the like; sulfonyl groups such as benzenesulfonyl, p-toluenesulfonyl and the like, carbamate forming groups such as benzyloxycarbonyl, p-chlorobenzyloxycarbonyl, p-methoxybenzyloxycarbonyl, and the like; substituted alkyl groups such as benzyl, triphenylmethyl, benzyloxymethyl and the like; and silyl groups such as trimethylsilyl and the like. Preferred suitable amino protecting groups are acetyl, methyloxycarbonyl, benzoyl, pivaloyl, allyloxycarbonyl, t-butylacetyl, benzyl, and benzyloxycarbonyl (Cbz) with t-butyloxycarbonyl (Boc) being more preferred.

As with any group of pharmaceutically active compounds, some groups are preferred in their end use application. A compound of Formula I wherein R is methyl or ethyl is preferred. A compound of Formula I wherein R is hydrogen is more preferred.

It is understood that compounds of the present invention may exist as stereoisomers. While all enantiomers, diastereomers, and mixtures thereof, are contemplated within the present invention, preferred embodiments are single enantiomers and single diastereomers.

The compounds of the present invention can be administered alone or in the form of a pharmaceutical composition, that is, combined with pharmaceutically acceptable carriers or excipients, the proportion and nature of which are determined by the solubility and chemical properties, including stability, of the compound selected, the chosen route of administration, and standard pharmaceutical practice. The compounds of the present invention, while effective themselves, may be formulated and administered in the form of their pharmaceutically acceptable salts, for convenience of crystallization, increased solubility, and the like.

Thus, the present invention provides pharmaceutical compositions comprising a compound of the Formula I and a pharmaceutically acceptable carrier, diluent or excipient.

A compound of Formula I may be administered by any route appropriate to condition being treated. For example, a compound of Formula I can be administered orally, by inhalation, subcutaneously, intramuscularly, intravenously, transdermally, intranasally, rectally, ocularly, topically, sublingually, buccally, and the like. Oral or topical administration is generally preferred for treatment of a herpes virus infection described herein. Ocular administration is preferred for the treatment of herpes simplex keratitis.

One skilled in the art of preparing formulations can readily select the proper form and mode of administration depending upon the particular characteristics of the compound selected, the disorder or condition to be treated, the stage of the disorder or condition, and other relevant circumstances (REMINGTON: THE SCIENCE AND PRACTICE OF PHARMACY, 19th Edition, Mack Publishing Co. (1995)).

The pharmaceutical compositions of the present invention are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

A compound of the present invention may be made by a process, which is analogous to one known in the chemical art for the production of structurally analogous compounds or by a novel process described herein. Such processes useful for the manufacture of a compound of Formula I as defined below are provided as further features of the invention and are illustrated by the following procedures in which, unless otherwise specified, the meanings of the generic radicals are as defined above. Techniques and reagents are well known and appreciated in the art.

Generally, a compound of Formula I may be prepared from a compound of Formula II where Pg represents a suitable amine protecting group (Scheme A).

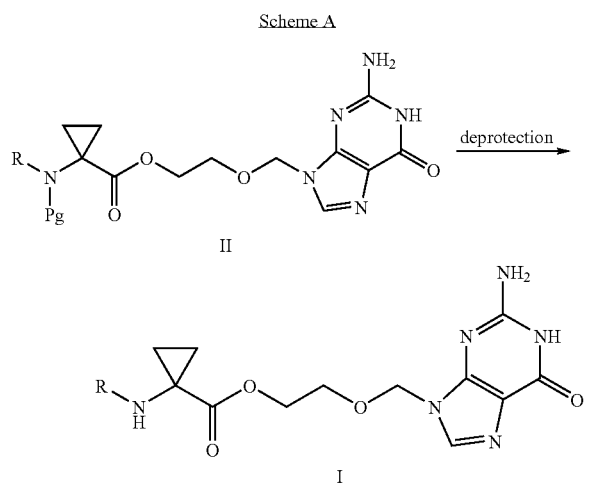

More specifically, a compound of Formula II is reacted with reagents suitable for removing the protecting group without adversely affecting the molecule. The conditions used to remove a protecting group depend on the chemical nature of the group as well as other functional groups of the compound, and are within the knowledge of the skilled artisan. For example, a compound of Formula II where Pg is t-butyloxycarbonyl is reacted within an acid such as trifluoroacetic acid in a suitable solvent such as methylene chloride to provide a compound of Formula I.

Generally, a compound of Formula II where Pg is an amino protecting group may be prepared from acyclovir and a compound of Formula III where Pg represents a suitable amino protecting group (Scheme B).

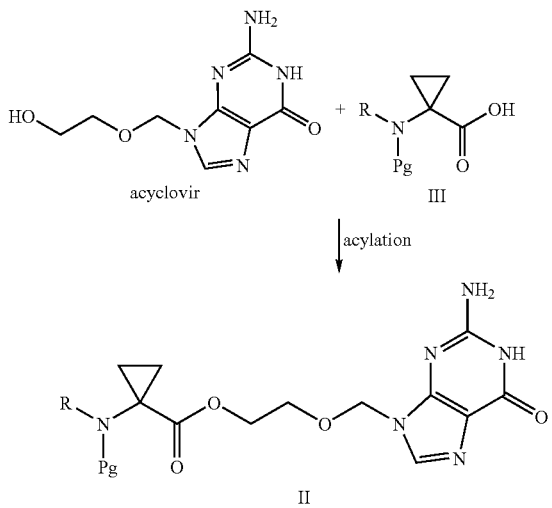

More specifically, acyclovir is combined with a compound of Formula III under acylation reaction conditions. For example, acylation reactions to transfer a compound of Formula III encompass an ester formation reaction similar to those which are conventionally conducted in the art and synthetic methods used therein can also be employed. For example, well known coupling reagents such as carbodiimides with or without the use of well known additives such as N-hydroxysuccinimide, 1-hydroxybelizotriazole, etc. may be used to facilitate ester formation. The reaction may also be performed in the presence of a base such triethylamine. The reaction is conveniently conducted in an inert aprotic solvent such as pyridine, dimethylformamide, dichloromethane, chloroform, 1,2-dichloroethane, acetonitrile, tetrahydrofuran and the like.

PREPARATION 1

Preparation of 1-tert-butoxycarbonylamino-cyclopropanecarboxylic acid 2-(2-amino-6-oxo-1,6-dihydro-purin-9-ylmethoxy)-ethyl ester

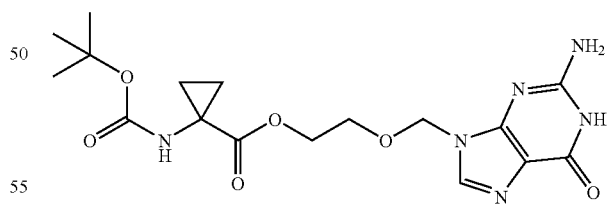

Combine acyclovir (0.50 g, 2.22 mmol) with t-Boc-aminocyclopropyl carboxylic acid (0.58 g, 2.89 mmol), 1-ethyl-3-(3-dimethylaminopropyl)-carbodiimide (0.64 g, 3.33 mmol) and 4-dimethylaminopyridine (0.05 g, 0.36 mmol) in dry N,N-dimethylformamide (3 mL). Add triethylamine (0.31 g, 3.11 mmol) and stir the resulting suspension at room temperature under nitrogen overnight. Cool to 0° C. and add 10 mL of a 0.3 M solution of hydrochloric acid to precipitate a white solid. Collect by vacuum filtration and wash with ether. The resulting solid is recrystallized from isopropanol to give product as a white solid. Yield: 93.7% MS (LC-MS): 409.3 (M+1). MS (LC-MS): 407.3 (M−1).

$^1$HNMR (d$_6$-DMSO): δ 0.97 (s 2H); 1.23-1.24 (d, 2H); 1.33 (s, 9H); 3.60 (s, 2H); 4.07 (s, 2H); 5.32 (s, 2H); 6.50 (s, 2H); 7.50 (s, 1H); 7.78 (s, 1H); 10.65 (s, 1H)

EXAMPLE 1

Preparation of 1-amino-cyclopropanecarboxylic acid 2-(2-amino-6-oxo-1,6-dihydro-purin-9-ylmethoxy)-ethyl ester trifluoroacetic acid salt

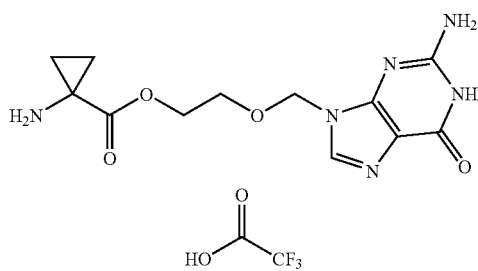

Suspend 1-tert-butoxycarbonylamino-cyclopropanecarboxylic acid 2-(2-amino-6-oxo-1,6-dihydro-purin-9-ylmethoxy)-ethyl ester (0.20 g, 0.49 mmol) of Preparation 1 in methylene chloride (2 mL) and stir at room temperature. Add trifluoroacetic acid (2 mL) dropwise and continue stirring. The suspension dissolves to give clear solution. Concentrate to dryness under vacuum. Triturate with ethyl acetate several times to isolate a white solid. Yield: 67.7% MS (ES+): 309.2 (M+1) MS (ES−): 307.2 (M−1)

$^1$HNMR (d$_6$-DMSO): δ 0.84-1.30 (m, 4H); 3.65 (t, 2H); 4.21 (t, 2H); 5.33 (s, 2H); 6.49 (s, 2H); 7.82 (s, 1H); 8.64 (s, 2H); 10.66 (s, 1H)

EXAMPLE 2

Preparation of 1-amino-cyclopropanecarboxylic acid 2-(2-amino-6-oxo-1,6-dihydro-purin-9-ylmethoxy)-ethyl ester

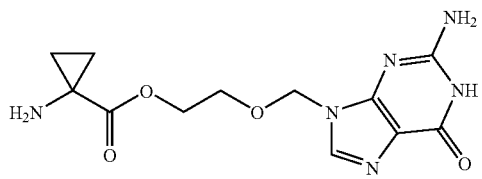

Dissolve 1-amino-cyclopropanecarboxylic acid 2-(2-amino-6-oxo-1,6-dihydro-purin-9-ylmethoxy)-ethyl ester trifluoroacetic acid salt (0.02 g, 0.05 mmol) of Example 1 in 1 mL methanol. Apply this solution to a 1 g Varian Mega Bond Elute® SCX column (Varian Part# 170532) pre-washed several times with methanol. Wash the column with 10 mL of methanol then elute the compound with 15 mL of a 2 M solution of ammonia in methanol. Concentrate in vacuo to obtain the desired free base as a white solid. MS (ES+): 309.2 (M+1)

$^1$HNMR (d$_6$-DMSO): δ 0.78 (q, 2H); 1.01 (q, 2H); 2.18 (s, 2H); 3.62 (m, 2H); 4.06 (m, 2H); 5.32 (s, 2H); 6.47 (s, 2H); 7.79 (s, 1H)

The present invention provides cyclopropanecarboxylate esters of acyclovir, a compound of Formula I, with unexpected stability to acid and base conditions. For example, a compound of Formula I wherein R is hydrogen shows a greater half-life compared to valacyclovir when incubated in aqueous solution at a pH of 6, 8 or 10 (Table A). This unexpected stability provides an advantage when formulating a pharmaceutical composition comprising an aqueous vehicle such as that of an ophthalmic solution.

EXAMPLE A

Hydrolytic stability of valacyclovir and 1-amino-cyclopropanecarboxylic acid 2-(2-amino-6-oxo-1,6-dihydro-purin-9-ylmethoxy)-ethyl ester trifluoroacetic acid salt Test samples of valacyclovir and 1-amino-cyclopropanecarboxylic acid 2-(2-amino-6-oxo-1,6-dihydro-purin-9-ylmethoxy)-ethyl ester trifluoroacetic acid salt (Example 1) are dissolved in buffered solutions of known pH at a concentration of 100 mcg/mL. Compound samples are prepared in 0.1 N hydrochloric acid for pH 1 and phosphate based buffer for pH2, 4, 6, 8 and 10. Stability is conveniently assessed using a semi-automated HPLC technique. Compound samples are loaded onto an HPLC autosampler incubated at 40° C. Samples are repeatedly injected on the HPLC at specific time intervals. The peak area of the compound samples are monitored by UV detection.

HPLC Method

The HPLC system consisted of an Agilent® 1100 autoinjector, pump, degasser and LV detector. A Waters® Atlantis dC-18 column (3 micron, 150×4.6 mm I.D.) is used to separate the degradation products from the compound sample. An isocratic reversed-phase system using ultraviolet detection is used to monitor the peak areas of the compound sample over a 24 hour period. The mobile phase composition is 5% acetonitrile and 95% water with 0.1% trifluoroacetic acid added to the mixture. The flow rate is 1.5 mL/min. The column temperature is 30 degrees Celsius and the injection volume was 10 μL. The UV detector is set at 256 nm and the run time was 9 minutes. Time points are analyzed every 2 hours for each buffer while being incubated at 40 degrees Celsius by the thermostat controlled autosampler.

Half-Life Calculation

The peak area of the compound sample is monitored over a 24 hour period at 2 hour intervals. The peak area of the compound sample is plotted versus time for each of the buffers tested. A first order calculation is used to determine the rate constant for each buffer based on the loss of peak area over time. The half-life, in hours, is calculated by dividing 0.693 by the rate constant (k). $t_{1/2}$ (hr)=0.693/k.

TABLE A

| | $t_{1/2}$ (hr) at 40° C. | | | | | |
|---|---|---|---|---|---|---|
| Sample | pH = 1 | pH = 2 | pH = 4 | pH = 6 | pH = 8 | pH = 10 |
| valacyclovir | >300 | >300 | >300 | 69.7 | 7.8 | 6.8 |
| Example 1 | >300 | >300 | >300 | >300 | 90.1 | 23.8 |

The invention claimed is:
1. A compound of Formula I

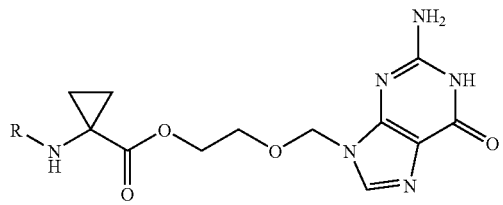

wherein
R is hydrogen or $C_1$-$C_4$ alkyl;
and pharmaceutically acceptable salts thereof.

2. A compound of claim 1 wherein R is hydrogen.

3. A compound of claim 1 selected from the group consisting of 1-amino-cyclopropanecarboxylic acid-2-(2-amino-6-oxo-1,6-dihydro-purin-9-ylmethoxy)-ethyl ester trifluoroacetic acid salt and 1-amino-cyclopropanecarboxylic acid-2-(2-amino-6-oxo-1,6-dihydro-purin-9-ylmethoxy)-ethyl ester.

4. A pharmaceutical composition comprising a compound of claim 1 and a pharmaceutically acceptable carrier, diluent or excipient.

5. A method of treating a herpes simplex or herpes zoster infection comprising administering to a patient in need thereof an effective amount of a compound of claim 1.

6. A method of treating a herpes simplex keratitis infection comprising administering to a patient in need thereof an effective amount of a compound of claim 1.

7. A process for preparing a compound of Formula I, or a pharmaceutically acceptable salt thereof, as claimed in claim 1 comprising:
a) preparing a compound of Formula II

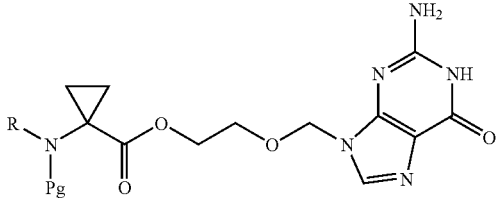

wherein R is hydrogen or $C_1$-$C_4$ alkyl, and Pg is an amino protecting group;

by acylating the compound acyclovir with a compound of Formula III

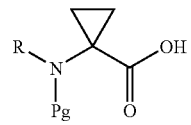

wherein Pg is an amino protecting group; and
b) preparing a compound of Formula I

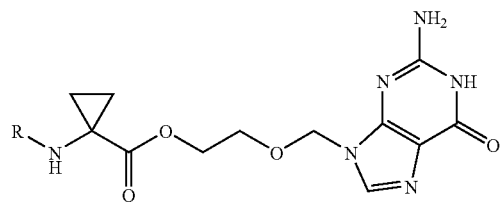

wherein R is hydrogen or $C_1$-$C_4$ alkyl;
by deprotecting a compound of Formula II

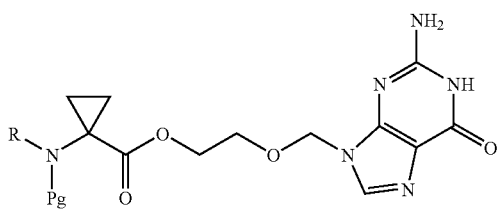

wherein R is hydrogen or $C_1$-$C_4$ alkyl, and Pg is an amino protecting group.

* * * * *